US008759282B2

(12) United States Patent
Stenberg et al.

(10) Patent No.: US 8,759,282 B2
(45) Date of Patent: Jun. 24, 2014

(54) WATER-SOLUBLE FILMS COMPRISING LOW-VISCOSITY ALGINATES

(75) Inventors: Kjell G Stenberg, Styckebruk (SE); Fredrik Hubinette, Uppsala (SE)

(73) Assignee: Uppsalagruppen Medical AB, Täby (SE)

( * ) Notice: Subject to any disclaimer, the term of this patent is extended or adjusted under 35 U.S.C. 154(b) by 847 days.

(21) Appl. No.: 12/158,472

(22) PCT Filed: Dec. 22, 2006

(86) PCT No.: PCT/SE2006/050626
§ 371 (c)(1),
(2), (4) Date: Nov. 24, 2008

(87) PCT Pub. No.: WO2007/073346
PCT Pub. Date: Jun. 28, 2007

(65) Prior Publication Data
US 2009/0221489 A1 Sep. 3, 2009

(30) Foreign Application Priority Data
Dec. 23, 2005 (SE) ...................................... 0502900

(51) Int. Cl.
A61K 31/167 (2006.01)
A61K 31/465 (2006.01)
A61K 9/70 (2006.01)
A61K 31/192 (2006.01)
A61K 31/616 (2006.01)
A61K 9/00 (2006.01)

(52) U.S. Cl.
CPC ............. *A61K 9/7007* (2013.01); *A61K 31/465* (2013.01); *A61K 31/167* (2013.01); *A61K 31/192* (2013.01); *A61K 31/616* (2013.01); *A61K 9/006* (2013.01)
USPC ....... 514/4.8; 514/343; 514/779; 106/205.01; 424/448; 536/3; 604/307

(58) Field of Classification Search
None
See application file for complete search history.

(56) References Cited

U.S. PATENT DOCUMENTS

| 4,029,757 | A | 6/1977 | Mlodozeniec et al. |
| 4,029,758 | A | 6/1977 | Mlodozeniec et al. |
| 4,031,200 | A | 6/1977 | Reif |
| 4,579,858 | A | 4/1986 | Ferno et al. |
| 4,713,239 | A | 12/1987 | Babaian et al. |
| 4,867,970 | A | 9/1989 | Newsham et al. |
| 4,876,092 | A | 10/1989 | Mizobuchi et al. |
| 4,900,552 | A | 2/1990 | Sanvordeker et al. |
| 5,047,244 | A | 9/1991 | Sanvordeker et al. |
| 5,229,164 | A | 7/1993 | Pins et al. |
| 5,346,701 | A | 9/1994 | Heiber et al. |
| 5,413,792 | A | 5/1995 | Ninomiya et al. |
| 5,446,070 | A | 8/1995 | Mantelle |
| 5,462,749 | A | 10/1995 | Rencher |
| 5,472,704 | A | 12/1995 | Santus et al. |
| 5,492,937 | A | 2/1996 | Bogentoft et al. |
| 5,508,043 | A | 4/1996 | Krishnamurthy |
| 5,599,554 | A | 2/1997 | Majeti |
| 5,626,866 | A | 5/1997 | Ebert et al. |
| 5,681,827 | A | 10/1997 | Field |
| 5,700,478 | A | 12/1997 | Biegajski et al. |
| 5,709,877 | A | 1/1998 | Della Valle et al. |
| 5,783,207 | A | 7/1998 | Stanley et al. |
| 5,804,209 | A | 9/1998 | De Ponti et al. |
| 5,958,443 | A | 9/1999 | Viegas et al. |
| 6,221,383 | B1 | 4/2001 | Miranda et al. |
| 6,926,888 | B1 | 8/2005 | Bjerkvig |
| 7,776,839 | B2 * | 8/2010 | Del Buono et al. ............. 514/54 |
| 2002/0121225 | A1 * | 9/2002 | Augello ..................... 106/205.1 |
| 2002/0127190 | A1 | 9/2002 | Zerbe et al. |
| 2003/0096012 | A1 | 5/2003 | Besse et al. |
| 2003/0143274 | A1 | 7/2003 | Viegas et al. |
| 2004/0115137 | A1 | 6/2004 | Verrall et al. |
| 2004/0131661 | A1 | 7/2004 | Auffret et al. |
| 2005/0011994 | A1 | 1/2005 | Sakurai et al. |
| 2005/0013847 | A1 * | 1/2005 | Ballard et al. ................ 424/439 |
| 2005/0019294 | A1 | 1/2005 | Modliszewski et al. |
| 2005/0069583 | A1 * | 3/2005 | Axford et al. ................. 424/464 |
| 2005/0214251 | A1 | 9/2005 | Pohl et al. |

FOREIGN PATENT DOCUMENTS

| CN | 1549702 A | 11/2004 | |
| EP | 0 469 745 | 2/1992 | |
| EP | 0 469 745 A2 * | 2/1992 | ............. A61L 15/16 |
| GB | 2 298 365 A | 9/1996 | |
| GB | 2398496 A | 8/2004 | |

(Continued)

OTHER PUBLICATIONS

A world of possibilities lies just below the surface. Protanal, Protacid, Protanal Ester Alginates (online). FMC BioPolymer (2003).*
A world of possibilities lies just below the surface. Protanal, Protacid, Ptotanal Ester Alginates säljbroschyr (online). *FMC BioPolymer* (2003).
Cha, D.S., et al. "Antimicrobial Films Based on Na-alginate and κ-carrageenan." *Lebensm.-Wiss. u.-Technol.* (2002) 35, pp. 715-719.
Al-Musa, S., et al. "Evaluation of parameters involved in preparation and release of drug loaded in crosslinked matrices of alginate." *Journal of Controlled Release* (1999) 57, pp. 223-232.

(Continued)

*Primary Examiner* — Suzanne Ziska
(74) *Attorney, Agent, or Firm* — Panitch Schwarze Belisario & Nadel LLP

(57) ABSTRACT

A film comprising as a film-forming agent an alginate salt of monovalent cation or a mixture of alginate salts containing at least one alginate salt of monovalent cation, the film-forming agent being such that a 10% aqueous solution thereof at a temperature of 20° C. has a viscosity of 100-1000 mPas, as measured at a shear rate of 20 rpm by use of a Brookfield viscometer with a spindle No. 2. A method of preparing the film. The film is useful for delivery of active ingredients to a mammal.

32 Claims, No Drawings

(56) References Cited

FOREIGN PATENT DOCUMENTS

| | | |
|---|---|---|
| JP | 63-303924 A | 12/1988 |
| JP | 05-148159 A | 6/1993 |
| JP | 2006-516616 A | 7/2006 |
| JP | 2007-525451 A | 9/2007 |
| RU | 2173139 C2 | 8/1999 |
| RU | 2229287 C2 | 5/2004 |
| RU | 2314796 C2 | 1/2008 |
| WO | 00 12066 A1 | 3/2000 |
| WO | 0166119 A2 | 9/2001 |
| WO | 03/015749 A1 | 2/2003 |
| WO | 03030882 A1 | 4/2003 |
| WO | 03030883 A1 | 4/2003 |
| WO | 03/043612 A1 | 5/2003 |
| WO | 03/070226 | 8/2003 |
| WO | 03/084516 A1 | 10/2003 |
| WO | 03092754 A1 | 11/2003 |
| WO | 2004/012720 | 2/2004 |
| WO | 2004041118 A2 | 5/2004 |
| WO | 2004067004 A1 | 8/2004 |
| WO | 2004/091528 | 10/2004 |

OTHER PUBLICATIONS

English translation of Office Action issued Nov. 10, 2010 in RU Application No. 2008130391/15.

English translation of an Office Action issued Aug. 14, 2012 in JP Application No. 2008-547188.

Extended EP Search Report issued Jan. 4, 2012 in counterpart EP Application No. 06 84 4046.

FMC BioPolymer, Material Safety Data Sheet—Protanol® LFR 5/60 Sodium Alginate (Dec. 9, 2008).

AIC, Specification Sheet—Guar Gum FCC ULV-50 (Edicol ULV-50) (Jun. 7, 2011).

Office Action issued Jan. 31, 2014 in EP Application No. 06844046.0.

* cited by examiner

WATER-SOLUBLE FILMS COMPRISING LOW-VISCOSITY ALGINATES

FIELD OF THE INVENTION

The present invention relates to a polymer film comprising an alginate polymer as well as to a method of preparing such a film. Furthermore, the invention relates to a composition in the form of an alginate film, comprising at least one biologically active substance, such as a therapeutically active substance, and to a method for the preparation of such a composition. Finally, the invention relates to the use of a polymer film comprising an alginate polymer for preparing a medicament, as well as to the use of a pharmaceutical film composition based on a polymer film comprising an alginate polymer for therapy.

BACKGROUND OF THE INVENTION

Alginate, the salt of alginic acid, is a linear polysaccharide naturally produced by brown seaweeds (Phaeophyceae, mainly *Laminaria*). It is composed of typically 100-3000 monomer residues linked together in a flexible chain. These residues are of two types, namely β-(1→4)-linked D-mannuronic acid (M) residues and α-(1→4)-linked L-guluronic acid (G) residues, respectively. The residues are epimers (D-mannuronic acid residues being enzymatically converted to L-guluronic acid residues after polymerization) and only differ at C5. However, in the polymer chain they give rise to very different conformations; any two D-mannuronic acid residues are $^4C_1$-diequatorially linked while the link connecting any two L-guluronic acid residues is a $^1C_4$-diaxial link, as illustrated in Formula I, herein below.

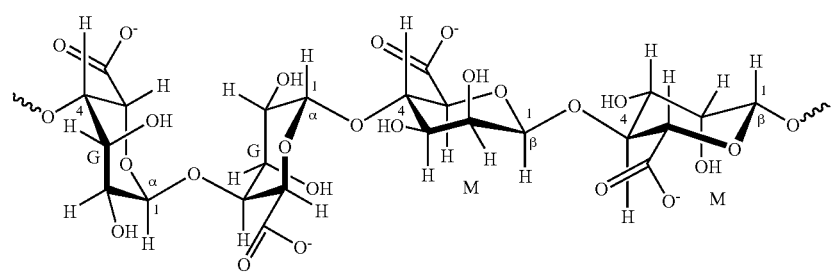

Formula I

The residues are organised in blocks of identical or strictly alternating residues (e.g. MMMMMM . . . GGGGGG . . . or GMGMGMGM . . . ).

Different monovalent and polyvalent cations, e.g. $Na^+$, $K^+$, $NH_4^+$, $Mg^{2+}$ and $Ca^{2+}$, are present as counter-ions to the negatively charged groups of the alginates.

Depending on factors such as mean polymer chain length, polymer composition and the cations present the flow characteristics of alginates vary widely, from free-flowing (low viscosity) to drip-free (high viscosity).

Alginates find uses in various fields, e.g. in pharmaceutical and food products where they are applied e.g. as thickeners, stabilizers and gelling agents. Their use in pharmaceutical compositions is mentioned in a number of patents and patent applications. Thus, U.S. Pat. No. 6,923,988 assigned to Lipocine, Inc. discloses a solid pharmaceutical composition for improved delivery of active ingredients. It is mentioned that the pharmaceutical composition may comprise alginate as a disintegrant.

U.S. Pat. No. 6,923,981 assigned to Warner-Lambert Company discloses fast dissolving orally consumable films for mouth hygiene. A listing of film forming agents is given and while sodium alginate is mentioned therein, pullulan is stated to be preferred and no example of an alginate film is given.

U.S. Pat. Nos. 6,656,493 and 6,740,332, both assigned to Wm. Wrigley Jr. Company disclose edible film formulations for mouth hygiene. The film formulations contain at least three types of film forming agents, viz. a maltodextrin, a hydrocolloid and a filler. The aim of the hydrocolloid is to provide thickness and decrease brittleness and alginates are mentioned as examples of a hydrocolloid.

US patent application No. 20050013847, assigned to FMC Corporation, relates to delivery systems comprising a homogenous, thermoreversible gel film, wherein the gel film comprises: a film forming amount of a water soluble thermoreversible alginate and optionally at least one of a plasticizer, a second film former, a bulking agent, and a pH controlling agent; and an active substance. The second film former is said to be optional but all examples show films comprising at least two film formers. The exemplified process for preparing the gel film comprises heating the alginate-containing mixture to an elevated temperature to form a homogeneous molten composition. The active substance is added either prior to or after formation of the molten composition and the molten composition containing the active substance then is cooled and further processed. It is mentioned that to modify the dissolution profile of the dosage forms the films can contain added components that can create solid dosage forms having immediate, enteric or delayed release capabilities.

U.S. Pat. No. 6,709,671, assigned to LTS Lohmann Therapie-Systeme AG discloses a monolayer film formed from a mucoadhesive composition which comprises at least one water-soluble polymer; a surfactant alone or in combination with at least one member selected from the group consisting of a polyalcohol and a plasticizer, or a polyalcohol and a plasticizer; and at least one cosmetic or pharmaceutical ingredient, for application into the mouth.

There are many ways of delivering active pharmaceutical ingredients (drugs) to the body (collectively termed formulations) depending on the type of drug and the disorder to be treated. For example, oral formulations such as tablets, capsules and lozenges; solutions of drugs in vials and pre-filled syringes for injection; topical formulations such as patches and ointments as well as nasal sprays. Other ways of delivering drugs, such as implanted pumps and slow-release depot formulations to be placed in the body, also exist. The formulation selected will typically have a marked influence on the therapeutic result of the drug, its side effects and the ease by which the patient can use the medication.

The most widely used drug formulation is the tablet that shall be swallowed for release of drug in the intestine. Tablets consist of a drug that is mechanically compressed together with a number of additional substances providing the structure and delivery properties of the tablet. Tablets need to be swallowed with a liquid such as water and some patients, e.g. children and elderly patients, may have difficulties in swallowing them.

A problem associated with oral tablets is that many drugs may be degraded during the passage through the acid environment of the stomach. When the drug has entered the intestine, drug is taken up into the blood stream via the portal vein into the liver where a large portion of the active pharmaceutical ingredients typically is metabolised to inactive chemicals by enzymes that normally take care of foreign substances in food, viz. the so-called first-pass metabolism.

These factors result in a significant delay before a positive therapeutic effect can be noted, leading to a risk of gastrointestinal side effects augmented by the need of administering considerably higher amounts of drug than would be needed by, for example, a direct injection of a drug solution into a vein.

Although injections provide a rapid pharmacological effect and reduce the risk of side effects, injections usually must be carried out by medically qualified staff at a medical centre or hospital, thus limiting the convenience of this administration form.

Nasal sprays may produce a rapid onset of action but is usually limited to local treatment of the respiratory tract. Other forms of formulations such as depots, patches or infusion devices are usually applied to address conditions where a sustained level of drug is required over longer time periods.

SUMMARY OF THE INVENTION

It is a general object of the present invention to provide a film that is adhesive to a moist surface of the body of a mammal and has a rapid dissolution profile in contact with the moist surface.

It is another general object of the invention to provide a film that is easy to prepare and does not require presence of additives, such as surfactants and disintegrants, in order to have the above indicated advantageous properties.

It is still a further object of the invention to provide a film formulation containing a biologically active substance, which may be a therapeutical or non-therapeutical substance, which film formulation may be used to deliver the biologically active substance to a mammal by application of the film formulation to a moist surface, such as a mucous membrane, of the mammal.

It is still a further object of the invention to provide a pharmaceutical film composition that is easy and convenient to self-administer, allows for a reduced dose of the active ingredient and thus less potential side effects and that can produce the desired pharmaceutical effect in a rapid and reliable manner.

It is another object of the present invention to provide a pharmaceutical film composition comprising one or several active ingredients permitting first-pass metabolism of the active ingredient(s) to be avoided.

It is another object of the present invention to provide a pharmaceutical film composition allowing for rapid onset of pharmacological action of one or several active ingredients.

It is another object of the invention to provide a pharmaceutical film composition allowing for the administration of active ingredients that are susceptible to destruction or deterioration in the gastro-intestinal tract.

It is still a further object of the invention to provide a pharmaceutical or non-pharmaceutical film composition allowing for easy and convenient administration of systemically and/or locally active ingredients to a mammal subject.

It is still another object of the invention to provide a pharmaceutical or non-pharmaceutical film composition that adheres firmly to the mucosa of the mouth of a mammal subject before it has been dissolved, diminishing the risk of losing it, either voluntarily or involuntarily, from the mouth of the subject.

It is another object of the invention to provide a pharmaceutical or non-pharmaceutical film formulation comprising active ingredients that are susceptible to deterioration at elevated temperatures, such as temperatures sensibly higher than room temperature.

It is a further object of the invention to provide a pharmaceutical or non-pharmaceutical film formulation capable of containing at least one active ingredient at a high level.

It is one object of the present invention to provide a method for preparing a film that may be used in a pharmaceutical or non-pharmaceutical film composition according to the invention.

The present invention is based on the surprising finding that by use of an alginate composition as defined herein, as a stand-alone film forming agent, a film that is adhesive to a moist surface of the body of a mammal and has a rapid dissolution profile in contact with the moist surface can be obtained.

Very advantageously, the film of the invention is bioadhesive, which means that when applied to a moist surface, such as a mucosa or a cornea, it adheres thereto, preferably within seconds.

Furthermore, in contact with a moist surface, such as a mucosa, the film of the invention is capable of dissolving within a time period of less than a few minutes, e.g. within less than 2 minutes.

Thus, according to one aspect of the invention a film is provided comprising as a film-forming agent an alginate salt of monovalent cation or a mixture of alginate salts containing at least one alginate salt of monovalent cation, the film-forming agent being such that a 10% aqueous solution thereof at a temperature of 20° C. has a viscosity of 100-1000 mPas, as measured at a shear rate of 20 rpm by use of a Brookfield viscometer with a spindle No. 2.

In one embodiment of the invention the film comprises at least one biologically active substance.

According to one other aspect of the invention, the use of a composition for preparing a film is provided, which composition comprises one or more active ingredients and, as film forming agent, an alginate salt of monovalent cation or a mixture of alginate salts of monovalent cation, characterised in that the film-forming agent is such that a 10% aqueous solution thereof at a temperature of 20° C. has a viscosity of 100-1000 mPas.

By use of the film-forming composition of the invention, a film formulation can be prepared, comprising a film capable of containing a high amount of one or several active ingredients, and having very desirable characteristics, as mentioned herein above. Thus, according to one aspect of the invention, a film formulation is provided comprising a biologically active ingredient, said film formulation being capable of adhering firmly to a moist surface of the body of a mammal and having a rapid dissolution profile in contact with the moist surface.

In one embodiment, the film composition is a pharmaceutical composition; in another embodiment the film composition is a non-pharmaceutical composition.

According to another aspect there is provided a method of preparing a film by preparing a composition comprising, as a film-forming agent, an alginate salt of monovalent cation or a mixture of alginate salts containing at least one alginate salt of monovalent cation, said film-forming agent being such that a 10% aqueous solution thereof at a temperature of 20° C. has a viscosity of 100-1000 mPas, as measured at a shear rate of 20 rpm by use of a Brookfield viscometer with a spindle No. 2, distributing the composition onto a solid surface, and permitting the composition to dry on the surface.

Generally, once the alginate salt composition of the invention has dissolved, the viscosity of the alginate solution varies only slightly with time. For example, viscosity was measured, as indicated herein above, within 10 minutes from dissolution of the alginate.

In one embodiment of the method of the invention, at least one biologically active substance is added to the film-forming composition.

According to still another aspect, the use of the film of the invention for preparing a medicament is provided.

According to still another aspect the invention provides a method of medical treatment of a mammal in need of such treatment by administering to said mammal a pharmaceutical film composition according to the invention.

Still further objects, aspects and embodiments of the invention will be apparent from the following description and the appended claims.

DETAILED DESCRIPTION OF THE INVENTION

According to one embodiment of the invention an alginate film is provided, based on a film forming composition comprising an alginate composition. The alginate composition to be used according to the present invention comprises at least one salt of alginic acid and one or several monovalent cations, preferably selected from sodium, potassium and ammonium ions. Most preferably the alginate composition of the invention comprises sodium alginate.

The alginate composition of the invention has a dynamic viscosity, as measured on a 10% aqueous solution thereof at a temperature of 20° C. with a Brookfield LVF viscometer (from Brookfield Engineering Laboratories, Inc.), using a spindle No. 2 at a shear rate of 20 rpm, of 100-1000 mPas, or 200-800 mPas, e.g. 300-700 mPas.

It should be noted that for the purpose of the present invention, and unless otherwise indicated, any % value is based on the weight of the components. In other words, e.g. 100 g of a 10% aqueous solution of an alginate contains 10 g of the alginate and 90 g of the other components, including water.

The alginate composition of the invention preferably has a mean guluronate (G) content of from 50 to 85%, preferably from 60 to 80%, most preferably from 65 to 75% by weight, a mean mannuronate (M) content of from 15 to 50%, preferably from 20 to 40%, most preferably from 25 to 35% by weight, and a mean molecular weight ranging from 30,000 g/mol to 90,000 g/mol, e.g. from 35,000 g/mol to 85,000 g/mol, such as from 40,000 g/mol to 70,000 g/mol or from 40,000 g/mol to 50,000 g/mol.

An exemplary alginate composition for use according to the present invention is Protanal® LFR 5/60, sold by FMC BioPolymer. Protanal® LFR 5/60 is a low molecular weight (low viscosity) sodium alginate extracted from the stem of *Laminaria hyperborea*.

As an example of an alginate that may be admixed with the alginate of monovalent cation in order to modify the viscosity of the alginate composition, mention may be made of Protanal® LF 10/60. This is a sodium alginate, sold by FMC BioPolymer, having a G/M % ratio of 65-75/25-35, a viscosity of 20-70, as measured on a 1% aqueous solution thereof at a temperature of 20° C. and at a shear rate of 20 rpm by use of a Brookfield viscometer with a spindle No. 2.

An increase in the mean molecular weight of the alginate polymer composition will result in an increase in the viscosity of the composition. The higher the viscosity, the lower the resulting release rate in alginate matrix systems. It is contemplated that the viscosity of the alginate composition may be adjusted by mixing any number of alginates having differing viscosities. It should be realized that if a mixture of alginates is used, then not all alginates, taken separately, need to have a viscosity within the specified ranges. However, to be useful for the purpose of the invention the alginate mixture resulting from the combination of more than one alginate species must be such as to have a viscosity value within the above indicated range.

Indeed, very advantageously the alginate-based film forming composition of the invention will result in a film having suitable dissolution properties in contact with a moist surface, such as a mucous membrane or a cornea. The dissolution characteristics of the film strongly influence the delivery of any active ingredient incorporated in the film to the body of the subject being treated. By the fast dissolving film of the invention it is possible to deliver, within a short period of time, i.e. essentially the time of dissolution of the film, i.e. preferably less than 2 minutes, an amount of the active ingredient into the body of the subject being treated. This will give a very advantageous concentration-vs.-time profile of the active ingredient within the body of the subject, permitting a high peak level of concentration to be obtained at a relatively lower total dose of the active ingredient, compared to other administration forms.

The film forming composition of the invention additionally may comprise any suitable excipient, such as one or more fillers or plasticizers. The plasticizer, when present, may be selected from e.g. polyethylene glycols, glycerol and sorbitol. A preferred plasticizer is sorbitol together with a small part of glycerol. A suitable amount of plasticizer is e.g. from 10 to 85 g, or from 30 to 70 g, e.g. from 50 to 60 g of plasticizer per 100 g of alginate.

The filler, when present, may be e.g. microcrystalline cellulose. A suitable amount of filler may be 0-20%, e.g. 5-10% by weight of the total pharmaceutical composition. However, it should be realised that it is a very advantageous feature of the invention that, apart from the alginate composition, no or very low level of other agents, such as fillers and plasticizers, influencing the physical characteristics of the film, are required. This feature allows for a high level of active ingredient to be included in the film composition of the invention. The active ingredient, when present in a high amount may by itself contribute to the advantageous properties of the film, such as suitable surface properties.

The mechanical properties of the film of the invention are very satisfactory, in particular the film is flexible, viz. it permits bending and folding without breaking, and has a very good tensile strength.

By use of the alginate-based film-forming composition as defined herein above a formulation according to the invention may be prepared, in the form of a film containing one or several biologically active ingredients.

The terms "biologically active ingredient", "active ingredient", "active substance" and "biologically active substance", are used interchangeably herein and are meant to include any substance having a desired biological activity or effect when administered to a mammal subject in accordance with the invention. The active ingredient/substance may be e.g. a therapeutically active ingredient. It also may be a biologically active ingredient that nonetheless is not generally considered as a pharmaceutical, e.g. a naturopathic preparation. As an example of a non-pharmaceutical active ingredient a stimulant or a nutraceutical may be mentioned, the latter generally defined as a substance that may be considered a food or part of a food and provides medical or health benefits, including the prevention and treatment of disease. Other biologically active substances may have both a therapeutical and non-therapeutical use.

The term "moist surface" as used herein preferably refers to a surface having a humidity preferably similar to that of a normally hydrated mucosa or cornea of a mammal subject, but also to a somewhat less humid surface such as found inside the ear.

The film formulation according to the invention preferably has a thickness of 0.1 to 2 mm, e.g. 0.2 to 1 mm, or from 0.2 to 0.6 mm, e.g. 0.5 mm.

The dosage unit may be of any suitable surface area, having regard to the concentration of the active ingredient within the film and the suitable dosage to be administered. As an example, a dosage unit having a surface area of from 1 $cm^2$ to 10 $cm^2$ may be selected when the film is to be applied within the oral cavity, while a smaller surface area, such as from 0.04 $cm^2$ to 1 $cm^2$ may be preferable when the film is to be applied in the eye. It will be within the knowledge of the skilled person to adapt the size and shape of the film dosage unit having regard to such parameters as the loading of the active ingredient(s) within the film, the required dosage, the site of administration to the body of the mammal subject etc. Also, it should be realized that the film dosage unit may have any appropriate shape to match the site of administration of the active ingredient, e.g. it may be rectangular, circular, oblong, oval etc.

The film formulation of the invention may comprise up to 85% by weight of the total formulation, of one or several active ingredients, e.g. up to 70% by weight, or up to 60% by weight, such as more than 20% by weight, or more than 30% by weight, e.g. more than 40% by weight. It however should be understood, that it is also contemplated that the film formulation of the invention may contain a very low level of active ingredient, if this is for any reason desired, e.g. if the active ingredient is to be delivered at a very small dosage. Thus, if preferable, the film formulation may contain active ingredient at a very low level, e.g. as low as 0.000001% by weight. The active ingredients may be selected from among all the presently known active substances and—in the future—from those that are presently unknown.

Thus, according to one aspect, the invention provides a unit dosage form in the form of a film having a selected surface area and thickness and containing an active ingredient at a defined concentration.

The active ingredient, leaving the dissolving film formulation of the invention to diffuse across the interface will reach the underlying tissue and the blood circulation, so as to enable not only local but also systemic administration while essentially avoiding first-pass metabolism and gastrointestinal digestion.

In addition to the active ingredient(s) the film formulation of the invention may comprise any physiologically (e.g. non-toxic at the added level) and/or pharmacologically acceptable additive, such as one or more flavouring agents (taste maskers) and/or colouring agents. Examples of flavouring agents are sorbitol, peppermint, orange flavouring, cherry flavouring, and cranberry extract. Examples of colouring agents are titanium dioxide and green or red food colour.

The pH of the film influences the rate of dissolution of the film. Generally, a film having a pH of from 6 to 9, e.g. from 8 to 9, has an optimal dissolution rate in contact with a moist surface.

The time of dissolution of a film according to the invention additionally is proportional to the film thickness and to the concentration of any particles in the film.

The skilled person, having regard to the desired time of dissolution for a given application, will be able to select a suitable film thickness by simply preparing films of a range of different thicknesses and testing said films for the dissolution time.

The active substance may be dissolved in the film solution, and/or may be non-dissolved and present therein e.g. as an emulsion or suspension. For example, the active substance may be present as a suspension of particles. In this case, as indicated herein above, the dissolution time will be somewhat longer due to the presence of particulate material in the film.

The skilled person will be able to determine the required thickness and unit dosage surface having regard to the level of particulate material and desired dissolution time, if necessary by performing simple tests.

In one embodiment of the invention, the film of the invention is provided with printed text matter or printed images, such as a brand name, a trade mark, a dosage indication, a symbol etc.

In one embodiment of the invention, the film formulation is a pharmaceutical film composition. "Pharmaceutical film composition", or "film pharmaceutical formulation" etc., as used herein are meant to include a composition according to the invention in the form of a film, comprising any of the biologically active ingredients as defined herein above, viz. any substance having a desired biological activity or effect when administered to a mammal subject, and which substance is useful in therapy.

The present invention also relates to the use of the pharmaceutical film composition of the invention for therapy, especially for nicotine therapy and analgetic therapy.

The very advantageous properties of the pharmaceutical formulation of the invention in the treatment of the disorders as mentioned herein above, as well as in the treatment of a number of other diseases that will readily present themselves to the person skilled in the art, will be obvious in the light of the description.

It should be noted that the pharmaceutical film composition according to the invention may be administered orally, nasally, rectally, intravaginally, topically, via wounds, the ears and the eyes of a patient. When administered via the eyes of a patient, the pharmaceutical film composition preferably is applied in the lower part of the eye directly to the cornea.

When the film is used as a means of administration of an active ingredient to the eye, this may be in replacement of e.g. eye drops or ointment, with obvious advantages. Indeed, eye drops may be difficult to administer so as to obtain a homogeneous and precise dosage. Also, ointments or other semi liquid formulations often are provided in packages, such as tubes or bottles, of quite short shelf life after opening due e.g. to bacterial spoilage, so that in many cases the package must be discarded while still not empty. The formulation of the invention, on the other hand is easy to apply in a precise and controlled dosage and may be provided in individual dosage packages, e.g. in blister packages, in air-tight envelopes or in any other suitable way, as will be obvious to the person skilled in the art.

The film of the invention can be used for delivery of a variety of substances to the body and for a range of different purposes.

Since the properties of the film are to adhere and dissolve rapidly and completely in contact with wet tissue, thereby releasing substance in solution, the most apparent application will be to deliver substances locally. Examples of local disorders are microbial infections in the upper respiratory tract and the genital tract, local inflammations in muscle or joints, skin disorders such as psoriasis, wound-healing or for local pain management.

However, compounds released from the film can also be taken up by the surrounding tissue and further distributed to the rest of the body via the bloodstream. This concept of rapid and efficient delivery to the bloodstream with little side effects has been shown for many substances by administrating substances rectally. However, the use of rectal formulations is not widely used possibly due to the inconvenience of administration and because of the tradition of using tablets for oral delivery.

Films can also be used to deliver certain substances to the body that are slowly taken up by the mucosa by, for example, releasing the substance to the oral cavity to be swallowed for a slow delivery to the gut.

To illustrate how the film-based delivery may be used for various disorders some examples are given below:

The film can be used to treat disorders in the stomach, where the substances are delivered from the "serum side" instead of from the gastric side or by uptake from the intestine and after liver passage. Typical disorders of the stomach amenable for film-delivery would be the acid-related symptoms such as gastritis, ulcers, reflux or infections caused by *Helicobacter pylori*. The types of substances that can be used include antimicrobial agents, histamine-2-receptor antagonists and proton pump inhibitors.

Because the film can deliver substances without the need to swallow water as with compressed tablets the invention is very useful for any medication where the patients' disorder render them unable to swallow and/or retain the medication in the body. Typical disorders are stroke, migraine, acute cardiac conditions and patients with obstructed digestion channel, sea-sickness, nausea and other situations where water is not available or cannot be swallowed. Many different types of substances may be used, among these CNS-acting substances such as serotonin receptor antagonists, prescription-free sea-sickness tablets and various anti-inflammatory substances.

Another disorder where the film technology described in this application can be used is obesity. Indeed, obese patients may be surgically treated (having parts of their stomach or the intestine removed) so as to reduce the absorption of substances from the gut. Delivery of medication by film preparations that have their effects on the nervous system would be unaffected by the patents gastro-intestinal operation history. An example of a type of substance that may be delivered in a film formulation according to the invention is sibutramin.

One interesting group of substances comprises the peptides and proteins. Substances of this group can not easily be taken in via the mouth and into the gut since they will be digested by enzymes (proteases and peptidases) present both in the stomach and the intestine. However, peptides and certain proteins may be taken up trough mucous tissue after release from the film since, in contrast to the gut; there is little peptidase activity in the mouth.

Since the film melts in the mouth, has no sugar additives and does not have to be swallowed it will be very suitable for oral diabetes therapy. Examples of suitable substance classes are the sulfoneurides, biguanid derivatives.

Patients that are very suitable candidates for film delivery of substances are the elderly people and children. Both these groups of patients are typically receiving more medication than the average and are often not able to self-medicate properly. Elderly people often get medication for sleep and for disorders typically associated with the ageing process such as dementia, Parkinson's disease, Alzheimer's disease, anxiety, depression and deficiencies of vitamins, nutrients and co-factors. The substance classes for this cohort of patients include CNS-acting drugs, antimicrobial agents and low molecular-weight cofactors.

In one embodiment of the invention, there is provided a method of preparing a film comprising, as a film-forming agent an alginate salt of monovalent cation or a mixture of alginate salts containing at least one alginate salt of monovalent cation, said film-forming agent being such that a 10% aqueous solution thereof at a temperature of 20° C. has a viscosity of 100-1000 mPas, as measured at a shear rate of 20 rpm by use of a Brookfield viscometer with a spindle No. 2, by preparing a solution of said film forming agent, distributing the solution onto a solid surface, and permitting the solution to dry on the surface.

To distribute a solution or composition onto a solid surface the solution or composition may simply be poured onto and/or spread evenly over the surface, e.g. by use of a draw-down blade or similar equipment.

A film formulation according to the present invention, containing at least one active ingredient, may be prepared e.g. by dissolving the active ingredient(s) in a suitable solvent; optionally adjusting the pH of the solution of active ingredient(s) to around neutral or alkaline pH; optionally adding plasticizer and microcrystalline cellulose, as well as any other suitable physiologically and/or pharmaceutically acceptable additive; adding an alginate salt composition which is such that a 10% aqueous solution thereof at a temperature of 20° C. has a viscosity of 100-1000 mPas as measured at a shear rate of 20 rpm by use of a Brookfield viscometer with a spindle No. 2; and processing the solution so as to obtain a film.

A suitable solvent for dissolving the active ingredient(s) may be e.g. water or an alcohol, e.g. methanol, ethanol, n-propanol, isopropanol, or t-butanol. Depending on the solubility and stability of the active ingredient(s), the solution thereof may be adjusted to a pH of 6-10, e.g. 8-10, or 8-9. To this end, any pH adjusting agent that is compatible with the intended use and with the other ingredients of the composition may be used, e.g. a suitable buffering system, aqueous sodium hydroxide, aqueous potassium hydroxide, sodium bicarbonate etc.

In one embodiment of a method of preparing a film formulation according to the invention comprising at least one active ingredient, the active ingredient(s) and the alginate(s) are simply dissolved together in a suitable solvent or mixture of solvents and the solution then is processed to a film and permitted to dry.

In another embodiment, the active ingredient is added to the alginate solution so as to give an emulsion or suspension of active ingredient in the alginate solution.

In one further embodiment, the film forming composition of the invention may comprise both dissolved and non-dissolved active ingredients. As an example, a film forming composition of the invention may comprise a combination of active ingredient dissolved in the alginate solution and active ingredient suspended in the solution.

After distributing the film-forming composition, optionally comprising any active ingredient, onto the solid surface, the composition is permitted to dry on the surface. The dry film formulation according to the invention preferably contains a homogeneous distribution of solubilised or suspended active ingredient(s). This contributes to the very advantageous delivery of the active ingredient through the moist surface to which the film is adhered. Thus, when adhered to a moist surface of the body, such as a mucosa or a cornea, the film will quickly dissolve and on dissolution of the film a concentration gradient of the active ingredient will rapidly be established at the interface of the film and the moist surface, giving rise to a diffusion of active ingredient across this interface. The active ingredient thereby will penetrate into the body, leaving the film as the latter dissolves.

In one embodiment, active ingredient is applied to the film of the invention after the forming of the film, which film may or may not comprise (another) active ingredient. Thus, an active ingredient may be applied e.g. as an aerosol spray onto a dry or wet film. An active ingredient also may be applied as a powder onto the film. Also, a flavouring agent may be applied in the same way.

The processing of the solution so as to obtain a dry film may comprise the steps of casting the solution on a support and allowing the wet film to dry. Drying preferably is performed at room temperature, e.g. 17-25° C., and under a normal atmosphere for a time period of e.g. 10 hours. Drying also may be performed under a dry atmosphere or under a lower than atmospheric pressure. In case the active ingredient(s) are not susceptible to thermal degradation, drying may be accelerated by raising the temperature, such as to 35° C.

The film so obtained may then be formed to the appropriate size and shape, such as by punching or cutting.

Optionally, before processing the solution into a film, any air bubbles may be removed e.g. by moderate heating or using a vacuum.

The film formulation according to the present invention presents e.g. the following advantages:
- the production of the films is reproducible;
- no plasticizer or filler is required;
- the film may be pleated and rolled without any risk of sticking, cracking or breaking;
- the film has a very good surface tensile (breaking) strength;
- a relatively large amount of active ingredient(s) may be included in the film;
- there is no need of heat treatment in the preparation process;
- the active ingredient(s) is/are metabolised quickly without any break-down in the stomach, enabling a lowered dose and less negative side effects, thereby, the film may be administered without any regard to the ingestion of meals;
- when applied in the mouth, there is a low risk of spitting the film out, as the films adheres to the mucous membranes in the mouth;
- no residues in the mouth after oral or buccal administration;
- text or numbers may be easily printed on the film;
- the film may be millimeter graded and cut into the desired length and form (e.g. circular, oval, square, rectangular etc.);
- the dose may easily be individually adapted to each patient;
- no need for coating with sugar, or any other covering, making the production simpler and less expensive; and
- the film is free of lactose (that may cause allergy reactions) and gelatine.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

By the expression "comprising/comprise" is meant "including/include but not limited to". Thus, other ingredients may be included.

EXAMPLE 1

A film formulation according to the invention was prepared by use of the following ingredients:
- 12 g sodium alginate corresponding to Protanal® LFR 5/60 having a viscosity of 300-700 mPas as a 10% aqueous solution and having a temperature of 20° C.;
- 80 g distilled water
- 3 g sorbitol
- 2 g glycerol
- 2 g cranberry extract
- 1 drop of green food colour
- sodium hydroxide
- 5 g paracetamol (as active pharmaceutical ingredient).

The active pharmaceutical ingredient was mixed with water and the pH adjusted to about 8-8.5 by addition of aqueous NaOH. The plasticizers, flavouring and colouring agents were added. The Protanal® LFR 5/60 was then added to the above-mentioned aqueous solution at room temperature in small portions and mixed until a homogenous solution was obtained.

The solution was applied to a 900 $cm^2$ glass plate as a support by means of a draw down blade for wet film application. The thickness was adjusted to 0.8-1 mm. The film was dried for about 12 hours at room temperature at atmospheric pressure, giving approximately a 30% loss of the film thickness.

The surface area of the film as prepared was 900 $cm^2$. From this film, dosage units of suitable size may be obtained. As an example, a film dosage unit of 6 $cm^2$ contains approximately 33 mg of paracetamol.

When placed inside the mouth, against the palate, the film dosage unit adhered practically immediately thereto and dissolved within 1.5 minutes without leaving any residue.

EXAMPLE 2

Proceeding generally as in EXAMPLE 1 a film formulation according to the invention was prepared by use of the following ingredients:
- 12 g sodium alginate corresponding to Protanal® LFR 5/60 having a viscosity of 300-700 mPas as a 10% aqueous solution and having a temperature of 20° C.;
- 80 g distilled water
- 3 g sorbitol
- 2 g glycerol
- 2 g cranberry extract
- 1 drop of green food colour
- sodium hydroxide
- 12 g paracetamol (as active pharmaceutical ingredient).

A film dosage unit of 6 $cm^2$ contains approximately 80 mg of paracetamol.

EXAMPLE 3

A film formulation according to the invention was prepared by use of the following ingredients:
- 12 g sodium alginate corresponding to Protanal® LFR 5/60 having a viscosity of 300-700 mPas as a 10% aqueous solution and having a temperature of 20° C.;
- 80 g distilled water
- 3 g sorbitol
- 2 g glycerol 2 g cranberry extract 1 drop of green food colour 6 g ibuprofen (as active pharmaceutical ingredient) dissolved in ethanol Ibuprofen was dissolved in a small volume of ethanol and the solution was mixed with water, resulting in precipitation of ibuprofen crystals. The plasticizers, flavouring and colouring agents were added. The Protanal® LFR 5/60 was then added, at room temperature in small portions and mixed until a homogenous milky white suspension of ibuprofen crystals was obtained.

The suspension was applied to a 900 cm$^2$ glass plate as a support by means of a draw down blade for wet film application. The thickness was adjusted to 0.8-1 mm. The film was dried for about 12 hours at room temperature at atmospheric pressure, giving approximately a 30% loss of the film thickness.

The surface area of the film as prepared was 900 cm$^2$. From this film, dosage units of suitable size may be obtained. As an example, a film dosage unit of 6 cm$^2$ contained approximately 40 mg of ibuprofen.

When placed inside the mouth, against the palate, the film dosage unit adhered practically immediately thereto and dissolved within 1.5 minutes without leaving any residue.

EXAMPLE 4

Proceeding generally as in EXAMPLE 1, but using aqueous bicarbonate buffer to regulate the pH of the film-forming composition, a film formulation according to the invention was prepared by use of the following ingredients:

12 g sodium alginate corresponding to Protanal® LFR 5/60 having a viscosity of 300-700 mPas as a 10% aqueous solution and having a temperature of 20° C.;

80 g aqueous sodium bicarbonate buffer pH 8-8.5.

3 g sorbitol 2 g glycerol 2 g cranberry extract 1 drop of green food colour sodium bicarbonate 5 g acetylsalicylic acid (as active pharmaceutical ingredient)

A film dosage unit of 6 cm$^2$ contains approximately 33 mg of acetylsalicylic acid.

EXAMPLE 5

Proceeding generally as in EXAMPLE 1 a film formulation according to the invention was prepared by use of the following ingredients:

12 g sodium alginate corresponding to Protanal® LFR 5/60 having a viscosity of 300-700 mPas as a 10% aqueous solution and having a temperature of 20° C.;

80 g distilled water 2 g cranberry extract 1 drop of green food colour sodium hydroxide 12 g paracetamol (as active pharmaceutical ingredient).

A film dosage unit of 6 cm$^2$ contains approximately 80 mg of paracetamol.

The film prepared without plasticizer is more brittle but dissolves very rapidly, in contact with a moist surface.

EXAMPLE 6

A film formulation according to the invention was prepared by use of the following ingredients:

11 g sodium alginate corresponding to Protanal® LFR 5/60 having a viscosity of 300-700 mPas as a 10% aqueous solution and having a temperature of 20° C.;

80 g aqueous potassium phosphate buffer pH 8.5, 0.1 M 2 g glycerol 3 g sorbitol 5.5 g nicotine bitartrate (as biologically active substance)

The active ingredient was mixed with the buffer. Glycerol and sorbitol were added. The Protanal® LFR 5/60 was then added to the thus prepared aqueous solution at room temperature in small portions and mixed until a homogenous solution was obtained.

The solution was applied to a 1200 cm$^2$ glass plate as a support by means of a draw down blade for wet film application. The wet film thickness was adjusted to approximately 0.3 mm. The film was dried for about 12 hours at room temperature at atmospheric pressure, giving approximately a 30% loss of the film thickness.

From this film, having a dry film thickness of approximately 0.2 mm, dosage units of 3 cm$^2$ were cut.

When placed inside the mouth, against the palate, the film dosage unit adhered practically immediately thereto and dissolved within 1.5 minutes without leaving any residue.

EXAMPLE 7

By use of the same film-forming composition and procedure as in EXAMPLE 6, a nicotine bitartrate film was prepared having a wet film thickness of approximately 0.15 mm, and a dry film thickness of approximately 0.1 mm. Dosage units of 3 cm2, when placed inside the mouth, dissolved within 45 seconds without leaving any residue.

EXAMPLE 8

Proceeding generally as in EXAMPLE 1 a film formulation according to the invention was prepared by use of the following ingredients:

11 g sodium alginate corresponding to Protanal® LFR 5/60 having a viscosity of 300-700 mPas as a 10% aqueous solution and having a temperature of 20° C.;

80 g distilled water 3 g sorbitol 2 g glycerol 6 g paracetamol (as active pharmaceutical ingredient).

Films of different dry film thicknesses were prepared and tested for dissolution time in contact with the moist surface in the palate of the mouth. The results are reported in Table 1, herein below.

TABLE 1

Dissolution time as a function of dry film thickness of a film of the invention

| Approximate dry film thickness (mm) | Dissolution time (seconds) |
| --- | --- |
| <0.05 mm | 1-2 |
| 0.05-0.1 mm | 5-8 |
| 0.1-0.15 mm | 10-12 |
| 0.15-0.3 | Approx. 20 |

The same films were also prepared with addition of peppermint oil as a flavouring agent. The flavouring agent efficiently masked the taste of paracetamol without notably influencing the film dissolution time.

In general, the delivery of the active ingredient by means of a film formulation according to the invention is surprisingly more efficient than by use of e.g. an oral formulation. As an example, a film unit dosage of an active ingredient as exemplified herein above shows a required therapeutic effect when delivered e.g. to a an adult human subject while containing an amount of active ingredient corresponding to only a fraction of that usually administered by the oral route in order to obtain the same level of therapeutic effect, such as analgesia.

EXAMPLE 9

Films obtained by use of an alginate having a viscosity according to the invention were compared with films obtained by use of alginates not according to the invention.

The following ingredients were used:
11 g alginate A, B or C (as defined in Table 1, below)
3 g glycerol
4 g sorbitol
80 g distilled water An aqueous solution of glycerol and sorbitol was prepared and the alginate was added under gentle stirring by rotating blades at the bottom of the mixing vessel. The solution was mixed to homogeneity, whereby additional water was added, if required.

The solution was applied to a 900 cm² glass plate as a support by means of a draw down blade for wet film application. The film thickness was adjusted to 1 mm. The film was dried for about 12 hours at room temperature at atmospheric pressure. Features of the films obtained by use of alginate A, B and C, respectively, are presented in Table 2.

TABLE 2

| Alginate | Product name | Viscosity* | Film characteristics | Dry film thickness (mm) | Dissolution time (min) |
|---|---|---|---|---|---|
| A (according to invention) | Protanal ® 5/60 LFR | <10** | Good wettability, adhesive to mucous membrane in mouth | ~0.3 | <2 |
| B (not according to invention) | Protanal ® LF120 M | 20-70*** | Poor wettability, not adhesive to mucous membrane in mouth | ~0.3 | 18-21 |
| C (not according to invention) | Protanal ® LF 200 M | 70-150*** | Poor wettability, not adhesive to mucous membrane in mouth | ~0.3 | >20 |

*Measured on a 1% solution at a shear rate of 20 rpm by use of a Brookfield viscometer with a spindle No. 2.
**Corresponding to a viscosity of 300-700 mPas as a 10% aqueous solution.
***Corresponding to a viscosity of more than 1000 mPas as a 10% aqueous solution.

EXAMPLE 10

Five compounds of different therapeutic use and of different chemical natures were selected to study whether they could be included into the film dosage form and with retained delivery properties (structural integrity of the film, adhere firmly to mucus, dissolve rapidly under moist conditions, release substance when dissolved.

Substance 1: Paracetamol (N-Acetyl-p-aminophenol or 4'-Hydroxiacetanilid)
pKa 9.5, Mw 151.2 only slightly soluble in water

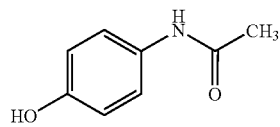

Substance 2: Acetylsalicylic acid; 2-Acetoxibensoesyra
pKa 3.5, Mw 180.16
1 g/100 g of water

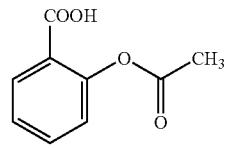

Substance 3: Ibuprofen; p-Isobutylhydratropic acid
pKa 4.8, Mw 206.29 slightly soluble in water

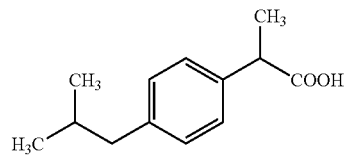

Substance 4: Nicotine; (S)-3-(1-Methyl-2-pyrrolidinyl) pyridine
pKa 8.5, Mw 162.23
liquid miscible with water

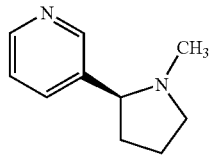

Substance 5: Lidocaine; Dietylaminoacet-2,6-xylidide
pKa 7.9, Mw 234.34
hydrochloride salt dissolves in water

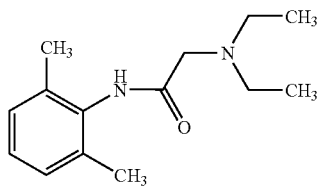 [SMILES: CCN(CC)CC(=O)Nc1c(C)cccc1C]

As can be seen by the chemical formulas, these compounds differ in size, pKa, solubility in water, type of ring systems, presence of basic (amine groups) and acidic (carboxylic) groups (all substance are shown as fully protonated) etc.

Paracetamol, nicotine and lidocaine have high pKa values, 7.9-9.5. Ibuprofen and acetylsalicylic acid have low pKa values, 3.5-4.8.

The pKa values show that the first three substances are basic whereas the two last compounds are acidic. Paracetamol and ibuprofen are reported to be only slightly soluble in water and the basic and acidic substances need to be at low or high pH.

In spite of the great variability in physical properties reflected in the different solubility properties of these substances all are possible to successfully formulate into a film formulation according to the invention with every positive property retained, indicating that the film formulations of the invention are useful essentially independently of the pKa value of the active substance to be incorporated therein. Generally, thus substances that have pKa values between about 1 and 14, such as between 2 and 12, or between 3 and 10, e.g. between 3.5 and 9.5, will be feasible to formulate with the film technology of the invention.

The invention claimed is:

1. A bioadhesive water-soluble film comprising, as a film-forming agent, an alginate salt of a monovalent cation or a mixture of alginate salts containing at least one alginate salt of a monovalent cation, the film-forming agent having a mean guluronate (G) content of from 50% to 85% by weight, a mean mannuronate (M) content of from 15% to 50% by weight, a mean molecular weight of from 30,000 g/mol to 90,000 g/mol and being such that an aqueous solution of 10% thereof at a temperature of 20° C. has a viscosity of 100 mPas to 1000 mPas, as measured at a shear rate of 20 rpm by use of a Brookfield viscometer with a spindle No. 2.

2. The bioadhesive film according to claim 1, wherein the monovalent cation is selected from the group consisting of $Na^+$, $K^+$ and $NH_4^+$.

3. The bioadhesive film according to claim 1, wherein the alginate salt of monovalent cation comprises from 25% to 35% by weight of β-D mannuronate.

4. The bioadhesive film according to claim 1, wherein the alginate salt of monovalent cation comprises from 65% to 75% by weight of α-D guluronate.

5. The bioadhesive film according to claim 1, further comprising a plasticizer.

6. The bioadhesive film according to claim 1, further comprising a filler.

7. The bioadhesive film according to claim 1, having a thickness of 0.1 mm to 2 mm.

8. The bioadhesive film according to claim 1, when in contact with a moist surface, dissolves within a time period of less than 2 minutes.

9. The bioadhesive film according to claim 1, further comprising at least one biologically active substance.

10. The bioadhesive film according to claim 1, further comprising at least one therapeutically active substance.

11. The bioadhesive film according to claim 1, further comprising at least one biologically active substance and/or therapeutically active substance selected from the group consisting of antimicrobial agents, histamine-2-receptor antagonists, proton pump inhibitors, serotonin receptor antagonists, anti-inflammatory substances, CNS-acting agents, peptides, proteins, nicotine, nicotine analogues and analgesics.

12. The bioadhesive film according to claim 11, wherein the biologically and/or therapeutically active substance is at a concentration from 0.000001% by weight to 85% by weight of the total weight of the composition.

13. The bioadhesive film according to claim 11, wherein the biologically and/or therapeutically active substance is at a concentration from 30% by weight to 80% by weight of the total weight of the composition.

14. The bioadhesive film according to claim 11, wherein the biologically and/or therapeutically active substance is at a concentration from 50% by weight to 70% by weight of the total weight of the composition.

15. The bioadhesive film according to claim 1, further comprising at least one pharmaceutically and/or physiologically acceptable additive.

16. The bioadhesive film according to claim 1, wherein said bioadhesive film is a single dosage unit.

17. A method of manufacturing a bioadhesive water-soluble film, said method comprising: a) dissolving a film-forming agent in a solvent or a mixture of solvents to obtain a liquid composition wherein the film-forming agent comprises an alginate salt of a monovalent cation or a mixture of alginate salts containing at least one alginate salt of a monovalent cation, the film-forming agent having a mean guluronate (G) content of from 50% to 85% by weight, a mean mannuronate (M) content of from 15% to 50% by weight, a mean molecular weight of from 30,000 g/mol to 90,000 g/mol and being such that an aqueous solution of 10% thereof at a temperature of 20° C. has a viscosity of 100 mPas to 1000 mPas, as measured at a shear rate of 20 rpm by use of a Brookfield viscometer with a spindle No. 2; b) distributing the composition onto a solid surface; and c) permitting the composition to dry on the surface.

18. The method according to claim 17, wherein the monovalent cation is selected from Na+, $K^+$ and $NH_4^+$.

19. The method according to claim 17, wherein the alginate salt of monovalent cation comprises from 25% to 35% by weight β-D mannuronate.

20. The method according to claim 17, wherein the alginate salt of monovalent cation comprises from 65 to 75% by weight of α-D guluronate.

21. The method according to claim 17, wherein the composition further comprises a plasticizer.

22. The method according to claim 17, wherein the composition further comprises a filler.

23. The method according to claim 17, wherein the composition further comprises at least one biologically active substance.

24. The method according to claim 17, wherein the composition further comprises at least one therapeutically active substance.

25. The method according to claim 17, wherein the composition further comprises at least one pharmaceutically and/or physiologically acceptable additive.

26. The method according to claim 17, wherein the composition further comprises at least one biologically active substance selected from the group consisting of antimicrobial agents, histamine-2-receptor antagonists, proton pump inhibitors, serotonin receptor antagonists, anti-inflammatory substances, CNS-acting agents, peptides, proteins, nicotine, nicotine analogues and analgesics.

27. The method according to claim 17, wherein the composition further comprises at least one biologically and/or therapeutically active substance at a concentration from 0.000001% by weight to 85% by weight of the total weight of the composition.

28. The method according to claim 17 wherein the composition further comprises at least one biologically and/or therapeutically active substance at a concentration from 30% by weight to 80% by weight of the total weight of the composition.

29. The method according to claim 17, wherein the composition further comprises at least one biologically and/or therapeutically active substance at a concentration is from 50% by weight to 70% by weight of the total weight of the composition.

30. The method according to claim 17, further comprising preparing the bioadhesive film in dosage units.

31. The method according to claim 17, further comprising administering to a mammal said bioadhesive film.

32. A bioadhesive water-soluble film prepared by a method comprising:
 a) dissolving a film-forming agent in a solvent or a mixture of solvents to obtain a liquid composition, wherein the film-forming agent comprises an alginate salt of a monovalent cation or a mixture of alginate salts containing at least one alginate salt of a monovalent cation, the film-forming agent having a mean guluronate (G) content of from 50% to 85% by weight, a mean mannuronate (M) content of from 15% to 50% by weight, a mean molecular weight of from 30,000 g/mol to 90,000 g/mol and being such that an aqueous solution of 10% thereof at a temperature of 20° C. has a viscosity of 100 mPas to 1000 mPas, as measured at a shear rate of 20 rpm by use of a Brookfield viscometer with a spindle No. 2;
 b) distributing the composition onto a solid surface; and
 c) permitting the composition to dry on the surface.

\* \* \* \* \*